(«12») United States Patent
Pozzi et al.

(10) Patent No.: US 8,247,426 B2
(45) Date of Patent: Aug. 21, 2012

(54) CRYSTALLINE IRINOTECAN HYDROCHLORIDE AND METHODS FOR ITS PREPARATION

(75) Inventors: Giovanni Pozzi, Rodano (IT); Paolo Ghetti, Rodano (IT); Gaetano Balsamo, Rodano (IT); Ettore Negri, Rodano (IT); Marco Alpegiani, Rodano (IT); Angelo Bedeschi, Rodano (IT); Roberta Pizzocaro, Rodano (IT)

(73) Assignee: Antibioticos S.p.A., Rodano (IT)

( * ) Notice: Subject to any disclaimer, the term of this patent is extended or adjusted under 35 U.S.C. 154(b) by 292 days.

(21) Appl. No.: 12/615,334

(22) Filed: Nov. 10, 2009

(65) Prior Publication Data

US 2010/0179180 A1 Jul. 15, 2010

(30) Foreign Application Priority Data

Nov. 11, 2008 (IT) .............................. MI2008A1984

(51) Int. Cl.
*A61K 31/4745* (2006.01)
*C07D 491/22* (2006.01)
(52) U.S. Cl. ........................................ 514/283; 546/48
(58) Field of Classification Search .................. 514/283; 546/48
See application file for complete search history.

(56) References Cited

U.S. PATENT DOCUMENTS 7,488,825 B2 * 2/2009 Shimizu et al. ................. 546/48

* cited by examiner

*Primary Examiner* — Charanjit Aulakh
(74) *Attorney, Agent, or Firm* — Rothwell, Figg, Ernst & Manbeck, P.C.

(57) ABSTRACT

Disclosed is a crystalline form of irinotecan hydrochloride (I) and processes for the preparation thereof from crude irinotecan hydrochloride or another polymorphic form of irinotecan. Said crystalline form is particularly suitable for industrial use, because it is easily filtered and possesses characteristics of high stability and purity.

(I)

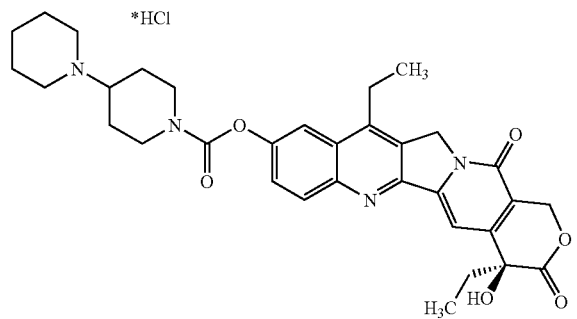

12 Claims, 3 Drawing Sheets

| Angle (°2θ) | Relative intensity (%) |
|---|---|
| 8.53 | 100 |
| 9.04 | 27.8 |
| 10.23 | 25.6 |
| 11.65 | 30.3 |
| 17.01 | 42.0 |
| 18.08 | 35.7 |
| 19.17 | 31.5 |
| 24.30 | 33.4 |

| Angle (°2θ) | Relative intensity (%) |
|---|---|
| 8.53 | 100 |
| 9.04 | 56.3 |
| 10.23 | 50.3 |
| 11.65 | 51.4 |
| 17.01 | 55.6 |
| 18.08 | 66.6 |
| 19.17 | 57.0 |
| 24.30 | 59.3 |

CRYSTALLINE IRINOTECAN HYDROCHLORIDE AND METHODS FOR ITS PREPARATION

FIELD OF INVENTION

The present invention relates to irinotecan I (chemical name: (S)-4,11-diethyl-3,4,12,14-tetrahydro-4-hydroxy-3,14-dioxo-1H-pyrano[3',4':6.7]-indolizino[1,2-b]quinolin-9-yl-[1,4'bipiperidine]-1'-carboxylate), in particular a novel crystalline form of its hydrochloride salt, methods for its preparation and pharmaceutical compositions containing it.

PRIOR ART

Irinotecan is a semisynthetic antitumoral compound derived from camptothecin (a natural alkaloid extracted from *Camptotheca acuminata* and *Nothapodytes foetida*) plants, which acts by inhibiting topoisomerase I; it is active against a variety of tumours, in particular colorectal, lung, stomach and pancreatic tumours. For treatment purposes it is generally used in the form of hydrochloride (I),

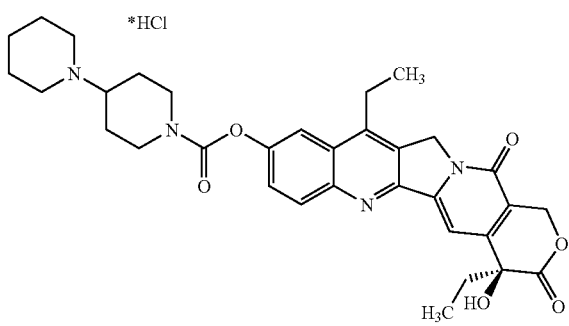

in a formulation marketed under the name of Camptosar®, an aqueous solution for injectable use with a concentration of 20 g/l. U.S. Pat. No. 4,604,463 discloses (example 37) the preparation of irinotecan hydrochloride as an amorphous solid (hereinafter called "form A") by freeze-drying an aqueous solution of irinotecan hydrochloride prepared from a suspension of irinotecan free base in water by adding 0.1N hydrochloric acid.

Sawada et al. (Chem. Pharm. Bull. Vol. 39, No. 6 1446-54, 1991) describe the preparation of irinotecan from camptothecin of natural origin, and crystalline irinotecan hydrochloride trihydrate (hereinafter called "form B"), known as CPT-11 (marketed as Camptosar®). Irinotecan hydrochloride trihydrate presents in the form of pale yellow needles or crystalline powder, and is obtainable by crystallisation from water, followed by drying and hydration in a chamber with controlled humidity until the maximum degree of hydration is reached. WO 03/074527 discloses another polymorphic form of irinotecan hydrochloride (hereinafter called "form C"), obtained by treating suspensions of irinotecan hydrochloride form A or irinotecan hydrochloride form B in acetone or acetonitrile; this polymorph does not contain hydration water. Four more polymorphs of irinotecan hydrochloride are disclosed in WO 2007/035709: the first (hereinafter called "form D") is obtained by crystallisation of irinotecan hydrochloride from ethanol, n-heptane and hydrochloric acid; the second (hereinafter called "form E") is obtained by crystallisation of irinotecan hydrochloride from ethanol and hydrochloric acid; the third (hereinafter called "form F") is obtained by crystallisation of irinotecan hydrochloride from methanol, ethyl acetate and hydrochloric acid; and the fourth (hereinafter called "form G") is obtained by crystallisation of irinotecan hydrochloride from ethanol, ethyl acetate and hydrochloric acid.

DESCRIPTION OF THE INVENTION

The object of the present invention is a crystalline form of irinotecan hydrochloride (hereinafter called "form H") characterised by an X-ray powder diffraction spectrum which shows the following significant peaks expressed as 2θ: 8.53, 9.04, 10.23, 11.65, 17.01, 18.08, 19.17 and 24.30. FIGS. 1 and 2 show the spectra of two H forms with different water contents; the crystals can contain up to 7 moles of water per mole of irinotecan, typically 1 to 5 moles, which are lost at high temperatures, as is typical of crystallisation water. Form H also presents an IR spectrum with the following significant peaks (cm$^{-1}$): 1746 (C=O lactone); 1719 (C=O carbamate); 1659 (C=O pyridone). In particular, FIG. 3 shows the IR spectrum of form H with a 13% water content.

The invention also relates to a process for the preparation of the crystalline form H comprising crystallisation of a polymorphic form of irinotecan hydrochloride from dichloromethane. In particular, a first process comprises the reaction between 7-ethyl-10-hydroxy-camptothecin and 1-chlorocarbonyl-4-piperidinopiperidine hydrochloride in pyridine, the concentration of the reaction mixture to a dry residue, and subsequent crystallisation by addition of dichloromethane. For this purpose, 7-ethyl-10-hydroxy camptothecin is reacted with 1 equivalent of 1-chlorocarbonyl-4-piperidinopiperidine hydrochloride in pyridine (15-70 volumes per gram of 7-ethyl-10-hydroxy camptothecin) to give irinotecan hydrochloride in solution. The synthesis can be conducted at a temperature of 20 to approx. 80° C. for the time required to complete the reaction, ie. 1-24 hours or more. Concentration of the reaction mixture then continues at low pressure until the solvent has been completely removed; the reaction mixture can be filtered before concentration if required. Concentration can be conducted at a temperature of 10 to approx. 80° C., and a residual pressure of under 50 mbars. The crystallisation of irinotecan hydrochloride to crystalline form H is conducted by dissolving the dry residue in dichloromethane at a temperature of 15-40° C. and subsequently concentrating the solution at low pressure until a concentrated solution is obtained. The dichloromethane used to dissolve the residue can be employed at the rate of 13-30 volumes per gram of 7-ethyl-10-hydroxy camptothecin, and the volume reached after concentration is usually 7-10 volumes per gram of 7-ethyl-10-hydroxy camptothecin. When concentration has been completed, the solution is left to cool at room temperature (15-35° C.) and the crystallisation of irinotecan hydrochloride form H is awaited. Crystallisation may begin spontaneously, or can be promoted by adding a primer of irinotecan hydrochloride form H. The crystallised mass is cured at the same temperature, and the solid is recovered by filtration with a suitable technique, such as gravity, pressure, suction, centrifugation or decanting.

A second process comprises dissolution of irinotecan base or amorphous irinotecan acetate in methanol, addition of hydrochloric acid in stoichiometric quantity or up to a 20% excess, concentration of the solution to a dry residue, and subsequent crystallisation by adding dichloromethane. For this purpose, irinotecan base or amorphous acetate is dissolved in 40-60 volumes of methanol per gram of irinotecan; hydrochloric acid is then added in gaseous form or as a solution in water or organic solvent, at a temperature of between approx. 10-50° C. In particular, 1 equivalent of concentrated hydrochloric acid can be used in the form of an aqueous solution with a concentration of 35-37% w/w, or a methanol solution with a concentration of 20% w/w; however, other concentrations can also be used. If dissolution is not complete at the end of the acid addition, complete dissolution of the product is awaited. The mixture can be heated to the boiling point of the solvent (65° C.) to promote dissolution, and the solution can be filtered if necessary. The irinotecan hydrochloride solution is then concentrated at low pressure until the solvent has been completely removed, so as to obtain a dry residue. Concentration can be conducted at a temperature of approx. 10-65° C., and a residual pressure of under 50 mbars. The crystallisation of irinotecan hydrochloride to crystalline form H is conducted by dissolving the dry residue in dichloromethane at a temperature of 15-40° C. and subsequently concentrating the solution at low pressure until a concentrated solution is obtained, followed by the procedure described for the first process.

A third process comprises dissolution of one of forms A-G of irinotecan in methanol, pyridine or mixtures of methanol and pyridine, concentration of the solution to a dry residue, and subsequent crystallisation by adding dichloromethane. For this purpose, irinotecan hydrochloride forms A-G or mixtures thereof are dissolved in methanol or pyridine or mixtures of methanol and pyridine at a temperature of approx. 10-65° C.; methanol can be used at the rate of 40-60 volumes per gram of irinotecan hydrochloride; pyridine can be used at the rate of 20-30 volumes per gram of irinotecan hydrochloride; and methanol and pyridine can be used in a 1:1 mixture at the ratio of 20-40 volumes per gram of irinotecan hydrochloride; however, other ratios can also be used. The mixture can be heated to the boiling point of the solvent to promote dissolution, and the solution can be filtered if necessary. The irinotecan hydrochloride solution is then concentrated at low pressure until the solvent has been completely removed, so as to obtain a dry residue. Concentration can be conducted at a temperature of approx. 10-65° C., and a residual pressure of under 50 mbars. The crystallisation of irinotecan hydrochloride to crystalline form H is conducted by dissolving the dry residue in 13-30 volumes of dichloromethane per gram of irinotecan hydrochloride at a temperature of 15-40° C., and subsequently concentrating the solution at low pressure until a concentrated solution (7-10 volumes of dichloromethane per gram of irinotecan hydrochloride) is obtained. This is followed by the procedure described for the first process.

Irinotecan hydrochloride in crystalline form H according to the invention has a purity greater than or equal to 99.5%, evaluated by the HPLC technique. This product can be dried in an oven under vacuum, static dryers or other drying machines. Drying can be conducted at a pressure of under 50 mbars and a temperature of 20-50° C. for the time required to reach the desired degree of purity (1-20 hours). When drying has been completed, form H can be packaged, or hydrated if necessary by exposure in an atmosphere with controlled humidity of 40-90% RH, at temperatures of 20-40° C., until the desired water content is obtained (KF range: 3-13%).

The high crystallinity of crystalline form H gives it chemical stability, a high degree of purity and excellent filterability characteristics. These characteristics are particularly advantageous on an industrial scale, because they allow high productivity in bulk; for example, irinotecan hydrochloride with high purity can easily be recovered directly from the reaction mixtures, or low-quality irinotecan can be purified without the use of onerous, unproductive chromatography techniques. Further characteristics of form H are ease of dissolution and high solubility in water at room temperature (over 20 g/l), thus allowing its use in the preparation of pharmaceutical compositions for therapeutic use, mixed with suitable excipients and/or vehicles, such as those described in WO 03/074527.

The invention is illustrated in greater detail in the figures and experimental part below.

EXPERIMENTAL PART

Test Methods

Figure 1:
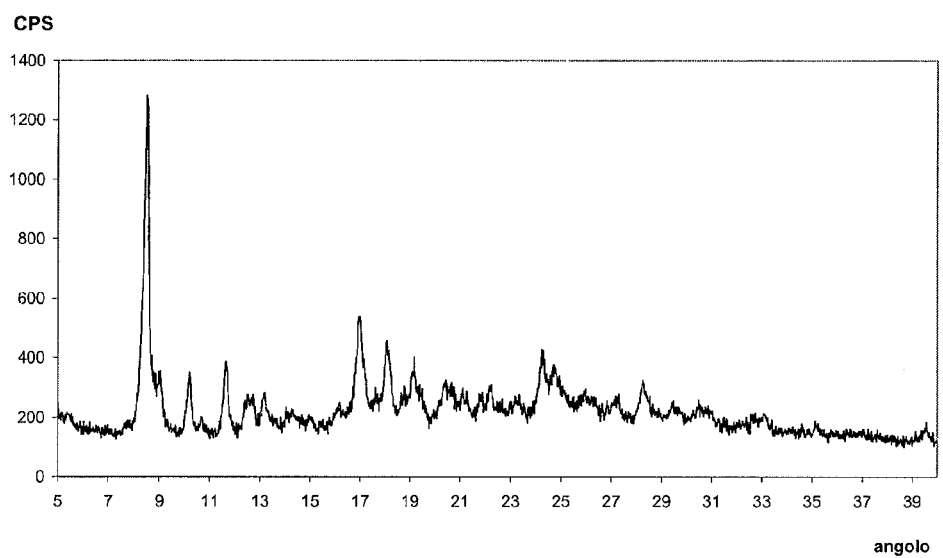
FIG. 1: X-ray powder diffractogram of irinotecan hydrochloride form H with a water content of 8.9%.
Figure 2:
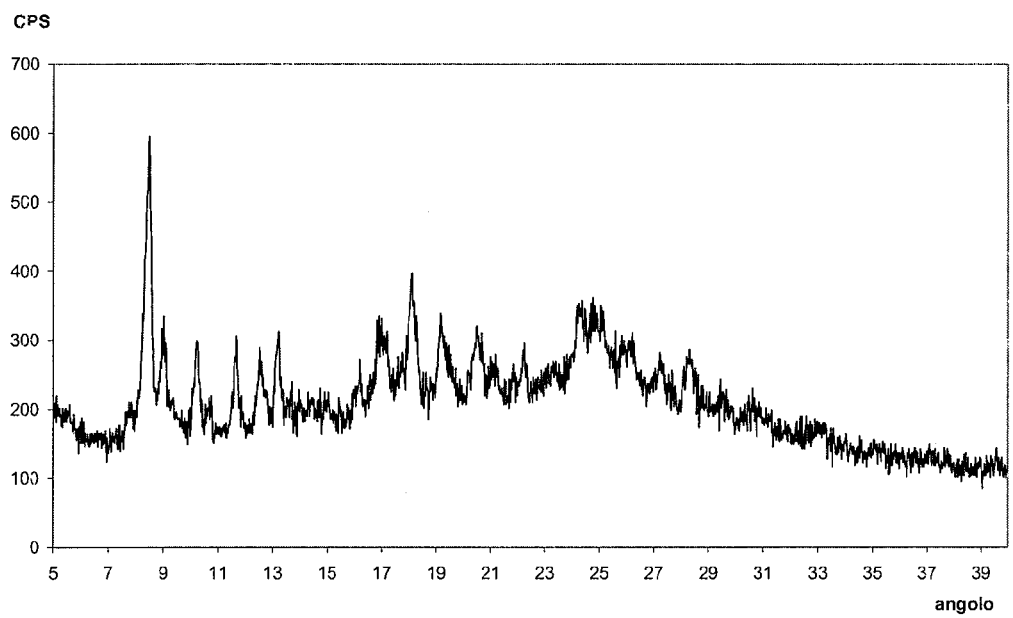
FIG. 2: X-ray powder diffractogram of irinotecan hydrochloride form H with a water content of 4.6%.
Figure 3:
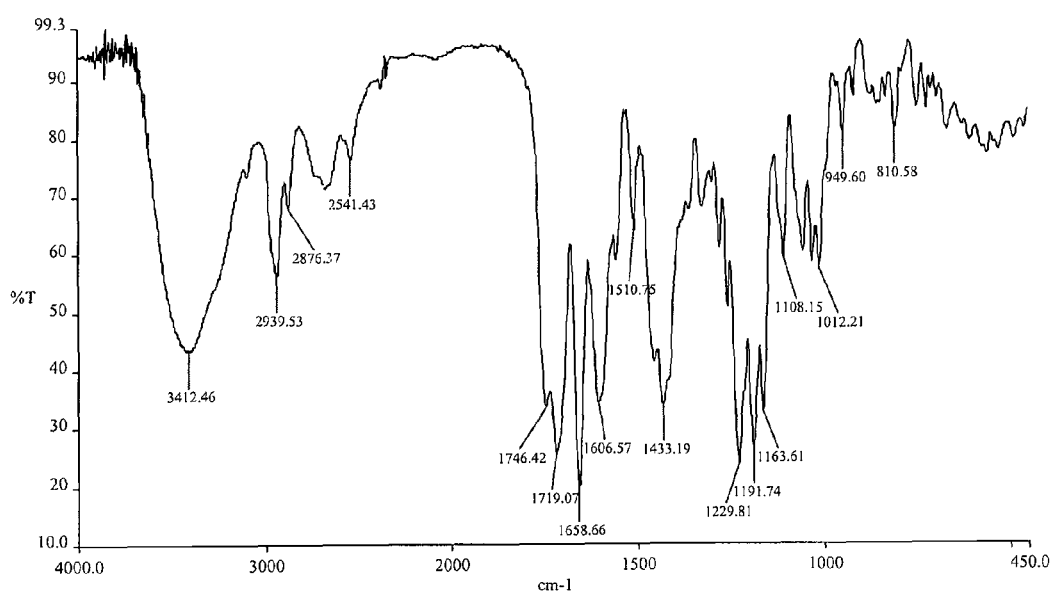
FIG. 3; IR spectrum (KBr tablet) of irinotecan hydrochloride form H with a water content of 13%.

The X-ray powder diffraction spectra were acquired with a PANalytical X'Pert Pro MPD diffractometer equipped with X'Celerator multichannel solid-state detector. The spectra were collected from 5 to 90° 2theta, with steps of approx. 0.016° 2theta, and a count time of 30 seconds per step. A 40 kV potential difference with a current of 40 mA, at the copper K-alpha wavelength (1,5418 A), was applied to the tube.

The IR spectra were acquired with a Perkin Elmer Spectrum 1000 spectrometer, 16 scans being acquired at the resolution of 4 $cm^{-1}$. The powder samples were mixed with potassium bromide to obtain mixtures containing 1% of the product. The mixture was pressed with a hand press.

Examples of Preparation of Form H

Example 1

Preparation of Form H from the Crude Product of Reaction Between 7-ethyl-10-hydroxy camptothecin and 1-chlorocarbonyl-4-piperidinopiperidine hydrochloride A suspension of 7-ethyl-10-hydroxy camptothecin (20.0 g) and 1-chlorocarbonyl-4-piperidinopiperidine hydrochloride (18.0 g) in pyridine (700 ml) was heated to 65° C. and left under stirring until the reaction was complete (HPLC analysis), which took 4 hours; at the end, the reaction mixture was a solution. The solvent was distilled at a pressure of under 50 mbars at 50° C. until a dry residue was obtained. The concentrated mass was taken up with dichloromethane (410 ml) and left under stirring at 35° C. until a solution was obtained. The solvent was distilled at a pressure of under 300 mbars at 35° C. until a concentrated solution (300 ml) was obtained. The temperature was adjusted to 25° C., and formation of the first crystals of the product was observed after approx. 30 minutes; after 15 hours' curing at 25° C., the crystallised mass was filtered through a Buchner funnel under suction, and the wet product was washed with dichloromethane (100 ml). After oven-drying under vacuum (residual pressure under 50 mbars), irinotecan hydrochloride form H (15.3 g) with high purity (HPLC purity=99.6%) and a 2.8% water content was obtained.

This product (13.0 g) was then hydrated by exposure in an atmosphere with 90% relative humidity; after 18 hours the weight proved stable (14.5 g; HPLC purity=99.6%; water=12%).

Example 2

Preparation of Irinotecan Form H from Irinotecan Base

A mixture of irinotecan free base (10.0 g) in methanol (500 ml) was heated to 50° C. 37% hydrochloric acid in water (1.4 ml) was dripped into the solution, and a solution was obtained. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C., until a concentrated solution (100 ml) was obtained, which was left to cool to 25° C.; the formation of the first crystals of the product was observed after approx. 30 minutes.

After 15 hours' curing at 25° C., the crystallised mass was filtered through a Buchner funnel under suction, and the wet product was washed with dichloromethane (35 ml). After oven-drying under vacuum (residual pressure under 50 mbars), irinotecan hydrochloride form H (8.2 g) with high purity (HPLC purity=99.6%) and a 4.6% water content was obtained.

Said product (5.0 g) was hydrated by exposure in an atmosphere with 75% relative humidity. After 18 hours the weight of the product proved stable (5.3 g). Irinotecan hydrochloride form H with high purity was obtained (HPLC purity=99.6%; water=9%).

Example 3

Preparation of Irinotecan Hydrochloride Form H from Amorphous Irinotecan (Form A)

A mixture of amorphous irinotecan acetate (10.0 g) in methanol (500 ml) was heated to 50° C.; 37% hydrochloric acid in water (1.3 ml) was then dripped into the solution, and a solution was obtained. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C., until a concentrated solution (100 ml) was obtained, which was left to cool to 25° C.; the formation of the first crystals of the product was observed after approx. 30 minutes. After 15 hours' curing at 25° C., the crystallised mass was filtered through a Buchner funnel under suction; the wet product was washed with dichloromethane (35 ml), and after oven-drying under vacuum (residual pressure under 50 mbars), irinotecan hydrochloride form H (7.4 g) with high purity (HPLC purity=99.6%) and a 3.5% water content was obtained.

Example 4

Preparation of Irinotecan Hydrochloride Form H from Irinotecan Hydrochloride Form B A mixture of irinotecan hydrochloride trihydrate form B (10.0 g) in methanol (500 ml) was heated to 50° C. to obtain a solution. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C., until a concentrated solution (100 ml) was obtained, which was left to cool to 25° C.; the formation of the first crystals of the product was observed after approx. 30 minutes. After 15 hours' curing at 25° C., the crystallised mass was filtered through a Buchner funnel under suction, and the wet product was washed with dichloromethane (35 ml). After oven-drying under vacuum (residual pressure under 50 mbars), irinotecan hydrochloride form H (8.0 g) with high purity (HPLC purity=99.6%) and a 4.3% water content was obtained.

Example 5

Preparation of Irinotecan Hydrochloride Form H from Irinotecan Hydrochloride Form C A mixture of irinotecan hydrochloride form C (10.0 g) in methanol (500 ml) was heated to 50° C., to obtain a solution. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C., until a concentrated solution (100 ml) was obtained, which was left to cool to 25° C.; the formation of the first crystals of the product was observed after approx. 30 minutes. After 15 hours' curing at 25° C., the crystallised mass was filtered through a Buchner funnel under suction, and the wet product was washed with dichloromethane (35 ml). After oven-drying under vacuum (residual pressure under 50 mbars), irinotecan hydrochloride form H (7.7 g) with high purity (HPLC purity=99.6%) and a 3.2% water content was obtained.

Example 6

Preparation of Irinotecan Hydrochloride Form H from Irinotecan Hydrochloride Form D A mixture of irinotecan hydrochloride form C (10.0 g) in methanol (500 ml) was heated to 50° C. to obtain a solution. The solvent was distilled at a pressure of under 50 mbars at 50° C. until a dry residue was obtained, and the concentrated mass was taken up with dichloromethane (150 ml) and left under stirring at 35° C. until a solution was obtained. The solvent was distilled at a pressure of under 300 mbars at 35° C. until a concentrated solution (100 ml) was obtained, which was cooled to 25° C.; the formation of the first crystals of the product was observed after approx. 30 minutes. After 15 hours' curing at 25° C., the crystallised mass was filtered through a Buchner funnel under suction. The wet product was washed with dichloromethane (35 ml), and after oven-drying under vacuum (residual pressure under 50 mbars), irinotecan hydrochloride form H (7.0 g) with high purity (HPLC purity=99.6%) and a 2.9% water content was obtained.

Example 7

Preparation of Irinotecan Hydrochloride Form H from Irinotecan Hydrochloride Form E A mixture of irinotecan hydrochloride form E (10.0 g) in methanol (500 ml) was heated to 50° C., and a solution was obtained. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C. until a concentrated solution (100 ml) was obtained, which was cooled to 25° C.; the formation of the first crystals of the product was observed after approx. 30 minutes. After 15 hours' curing at 25° C., the crystallised mass was filtered through a Buchner funnel under suction. The wet product was washed with dichloromethane (35 ml), and after oven-drying under vacuum (residual pressure under 50 mbars), irinotecan hydrochloride form H (7.2 g) with high purity (HPLC purity=99.6%) and a 4.0% water content was obtained.

Example 8

Preparation of Irinotecan Hydrochloride Form H from Irinotecan Hydrochloride Form F A mixture of irinotecan hydrochloride form F (10.0 g) in methanol (500 ml) was heated to 50° C., and a solution was obtained. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C. until a concentrated solution (100 ml) was obtained, which was cooled to 25° C.; the formation of the first crystals of the product was observed after approx. 30 minutes. After 15 hours' curing at 25° C., the crystallised mass was filtered through a Buchner funnel under suction. The wet product was washed with dichloromethane (35 ml), and after oven-drying under vacuum (residual pressure under 50 mbars), irinotecan hydrochloride form H (7.5 g) with high purity (HPLC purity=99.6%) and a 3.7% water content was obtained.

Example 9

Preparation of Irinotecan Hydrochloride Form H from Irinotecan Hydrochloride Form G A mixture of irinotecan hydrochloride form G (10.0 g) in methanol (500 ml) was heated to 50° C., and a solution was obtained. The solvent was distilled at a pressure of under 50 mbars at 50° C. until a dry residue was obtained. The concentrated mass was taken up with dichloromethane (150 ml) and left under stirring at 35° C. until a solution was obtained. The solvent was distilled at a pressure of under 300 mbars at 35° C. until a concentrated solution (100 ml) was obtained, which was cooled to 25° C.; the formation of the first crystals of the product was observed after approx. 30 minutes. After 15 hours' curing at 25° C., the crystallised mass was filtered through a Buchner funnel under suction. The wet product was washed with dichloromethane (35 ml), and after oven-drying under vacuum (residual pressure under 50 mbars), irinotecan hydrochloride form H (7.1 g) with high purity (HPLC purity=99.6%) and a 3.5% water content was obtained.

The invention claimed is:

1. A crystalline form H of irinotecan hydrochloride I

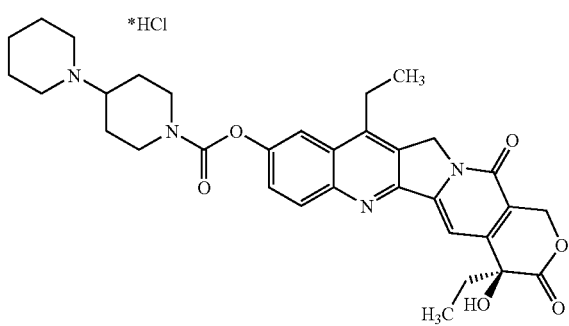

(I)

characterized by an X-ray powder diffraction spectrum which presents the following significant peaks expressed as 2θ: 8.53, 9.04, 10.23, 11.65, 17.01, 18.08, 19.17 and 24.30, and by an IR spectrum which presents the following absorption peaks (cm$^{-1}$): 1746 (C=O lactone); 1719 (C=O carbamate); 1659 (C=O pyridone).

2. The crystalline form H of irinotecan hydrochloride I of claim 1, containing up to 7 moles of water per mole of irinotecan hydrochloride.

3. The crystalline form H of irinotecan hydrochloride I of claim 2, containing 1 to 5 moles of water per mole of irinotecan hydrochloride.

4. A process for the preparation of the crystalline form H of claim 1, comprising of crystallizing irinotecan base, amorphous irinotecan, 7-ethyl-10-hydroxy-camptothecin or a polymorphic form of irinotecan hydrochloride from dichloromethane.

5. The process of in claim 4, comprising reacting 7-ethyl-10-hydroxy-camptothecin and 1-chlorocarbonyl-4-piperidinopiperidine hydro-chloride in pyridine to form a reaction mixture, concentrating the reaction mixture to a dry residue, and subsequently crystallizing by adding dichloromethane to the dry residue.

6. The process of claim 4, comprising dissolving irinotecan base or amorphous irinotecan acetate in methanol, adding hydrochloric acid in stoichiometric quantity or up to a 20% excess, concentrating the solution to a dry residue, and subsequently crystallizing by adding dichloromethane to the dry residue.

7. The process of claim 4, comprising dissolving one of forms A-G of irinotecan in methanol, pyridine or mixtures of methanol and pyridine, concentrating the solution to a dry residue, and subsequently crystallizing by adding dichloromethane to the dry residue.

8. A pharmaceutical composition containing the crystalline form H of irinotecan hydrochloride of claim 1, mixed with suitable excipients and/or vehicles.

9. A pharmaceutical composition of claim 8, in the form of an injectable solution.

10. A method of preparing a composition comprising a crystalline form H of irinotecan hydrochloride, comprising mixing the crystalline form H of irinotecan hydrochloride of claim 1 with at least one pharmaceutically suitable excipient and/or vehicle.

11. The method of claim 10, wherein the composition is an injectable solution.

12. The process of claim 4, wherein said polymorphic form of irinotecan hydrochloride is selected from one of forms A-G of irinotecan.

* * * * *